United States Patent [19]

Sanders

[11] Patent Number: 4,534,209
[45] Date of Patent: Aug. 13, 1985

[54] ATMOSPHERIC CONSISTOMETER

[76] Inventor: Howard E. Sanders, 49 S. 85th East Ave., Tulsa, Okla. 74112

[21] Appl. No.: 532,363

[22] Filed: Sep. 15, 1983

[51] Int. Cl.³ ............................................. G01N 11/14
[52] U.S. Cl. ............................................. 73/59; 73/54
[58] Field of Search ................................. 73/59, 60, 54

[56] References Cited

U.S. PATENT DOCUMENTS

| | | | |
|---|---|---|---|
| 2,382,979 | 8/1945 | Demb | 73/59 |
| 2,410,385 | 10/1946 | Loukomsky et al. | 73/59 |
| 2,491,639 | 12/1959 | Bechtel et al. | 73/59 |
| 2,679,157 | 5/1954 | Carpenter | 73/59 |
| 2,953,016 | 9/1960 | Seitz, Jr. | 73/60 |
| 4,175,425 | 11/1979 | Brookfield | 73/59 |

OTHER PUBLICATIONS

V. P. Zhereb et al, Automic Viscosimeter for Investigation of Melts, Instrument Exp. Tech.–1979.

Primary Examiner—Stewart J. Levy
Assistant Examiner—Hezron E. Williams
Attorney, Agent, or Firm—Head, Johnson & Stevenson

[57] ABSTRACT

An apparatus is provided for determining the consistency of a cement slurry under varying temperature and time conditions. A liquid containing vessel includes a shaft extended from the bottom rotated by a motor supported exteriorally of the vessel. Within the vessel a cylindrical slurry cup is removeably supported for rotation by the shaft in an upright coaxial manner. Received within the slurry cup is a paddle having vertical portions in proximity to the interior wall of the slurry cup. The paddle has an upwardly extending coaxial shaft. Mounted in an opening in the top of the vessel is a potentiometer cup having a potentiometer in a plane perpendicular the shaft axis. A coiled spring also in a plane perpendicular the shaft has one end affixed to the paddle shaft and the other end secured to the potentiometer cup. A wiper arm extends from the shaft to the potentiometer. A volt meter connected to the potentiometer measures the displacement of the paddle shaft in response to the rotation of the slurry cup, which rotation is resisted by the coiled spring. The consistency of the slurry within the cup is reflected by the volt meter reading.

3 Claims, 7 Drawing Figures

ATMOSPHERIC CONSISTOMETER

SUMMARY OF THE INVENTION

In some applications of slurries formed of a liquid base, such as water, and a solid component, such as cement, it is important to know the consistency of the slurry as a function of time and temperature. This is particularly true in the petroleum industry. The first length of pipe, usually called the surface pipe or surface casing, inserted into the earth in the process of drilling a well is cemented into position. This is accomplished by pumping cement down the interior of the pipe to flow to the bottom of the pipe and up the annular area between the exterior of the pipe and the borehole. In other applications, in addition to cementing the surface pipe in position, it is necessary to cement the annular area between a casing and a subterranean formation to block the flow of fluids or gases from one formation area to another. In these applications the cement slurry must be pumped to substantial depths in the earth. This procedure takes time and subjects the slurry to high temperatures. For instance, if the depth of a casing to be cemented is 1,000-feet it only takes approximately seven minutes for cement to be pumped from the surface to the bottom. The temperature at the bottom may be only approximately 80°. On the other hand, if the depth to which the cement slurry must be pumped is 16,000-feet, it may take approximately 60 minutes for the cement to reach the bottom after it is pumped from the surface. In addition the bottom hole temperature may be approximately 248°. Thus there is a great deal of difference in the characteristics required of a cement slurry to be pumped at a relatively shallow depth compared to a relatively deep depth.

It can be seen that if a slurry is employed which solidifies to a non-pumpable condition in less than 60 minutes, an attempt to pump the slurry to a depth of 16,000-feet may result in complete failure. On the other hand if the slurry remains in a highly liquid state for a long period of time and is used in an attempt to set surface pipe wherein the total depth is not great, an unnecessary length of time is required for the setting to be accomplished.

These are merely rudimentary examples of reasons it is important in the petroleum industry for operators to know the consistency of a cement slurry under varying time and temperature conditions.

Techniques have been developed and approved by the American Petroleum Institute for measuring the consistency of cement slurries utilizing consistometers which employ a rotating cylinder having a paddle therein, the paddle being restricted in its rotation by a coil spring. By measuring the torque applied by the slurry filled cup to the paddle the consistency of the slurry can be established.

The present invention is directed towards an improved apparatus for conducting consistometer measurements. The apparatus includes a liquid containing vessel having a bottom, top and sidewalls. The bottom and top have aligned openings. Positioned in the opening in the bottom is a shaft which is sealed. On the bottom of the shaft, exterior of the vessel, is a sheave connected by a belt to a motor driven sheave so that the shaft is rotated. Within the vessel, at the upper end of the shaft is a flange.

Removeably seated on the flange and rotatably coupled to it is an upright open top cylindrical slurry cup which receives the slurry to be tested. Positioned within the slurry cup is a paddle having vertical portions which are in close proximity to the vessel internal cylindrical wall. The paddle has a shaft which extends upwardly coaxial with the cup cylindrical axis. Received in the opening in the top of the vessel is a potentiometer cup which in turn has a central opening receiving the paddle shaft. Within the cup is a circular potentiometer. Surrounding the shaft within the cup is a coiled spring having one end affixed to the shaft and the other end affixed to the potentiometer cup.

A voltmeter is connected to a voltage source and to leads from the potentiometer. A wiper arm is affixed to the paddle shaft and engages the potentiometer and a lead extends from it to the voltmeter. By measurement of the position of the wiper arm on the potentiometer, the rotational displacement of the paddle shaft indicates the consistency of the slurry within the cup.

A means is provided for varying the temperature of the fluid within the vessel to thereby control the temperature of the slurry. By plotting the consistency versus time and temperature, the characteristics of the slurry can be established.

The instrument provides a simple and expedient means of conducting tests for consistency of particular cement slurry compositions to enable the user to predict their behavior when used in oil wells.

DETAILED DESCRIPTION OF THE PREFERRED EMBODIMENT

Figure 1:
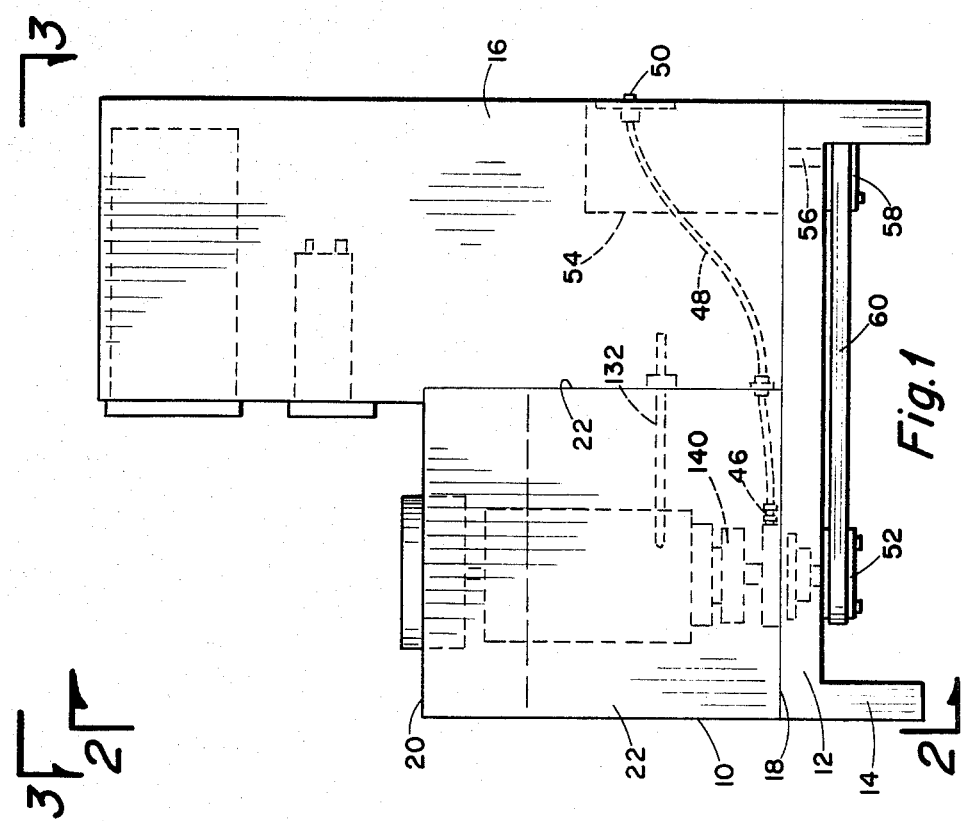
FIG. 1 is an elevational side view of an apparatus embodying the principles of this invention for measuring the consistency of a cement slurry under varying times and temperatures.
Figure 3:
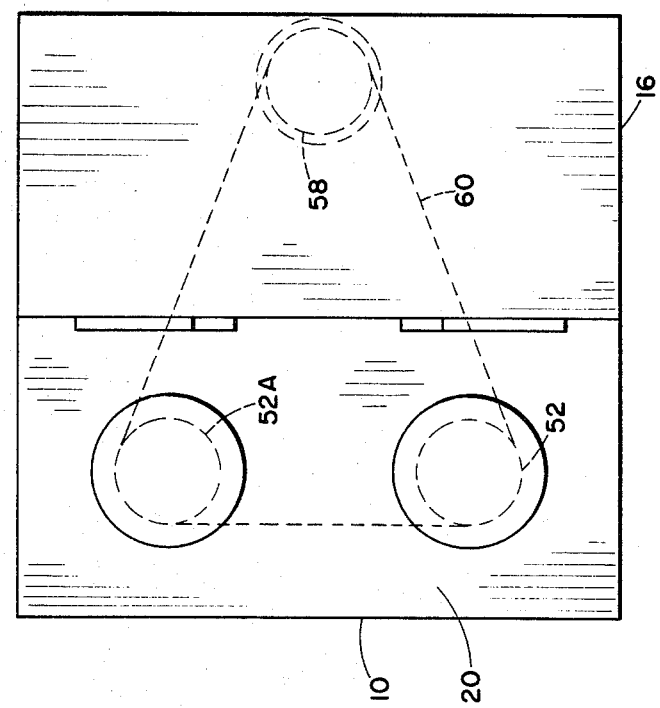
FIG. 3 is a top view showing the general layout of the apparatus as employed in the invention.
Figure 2:
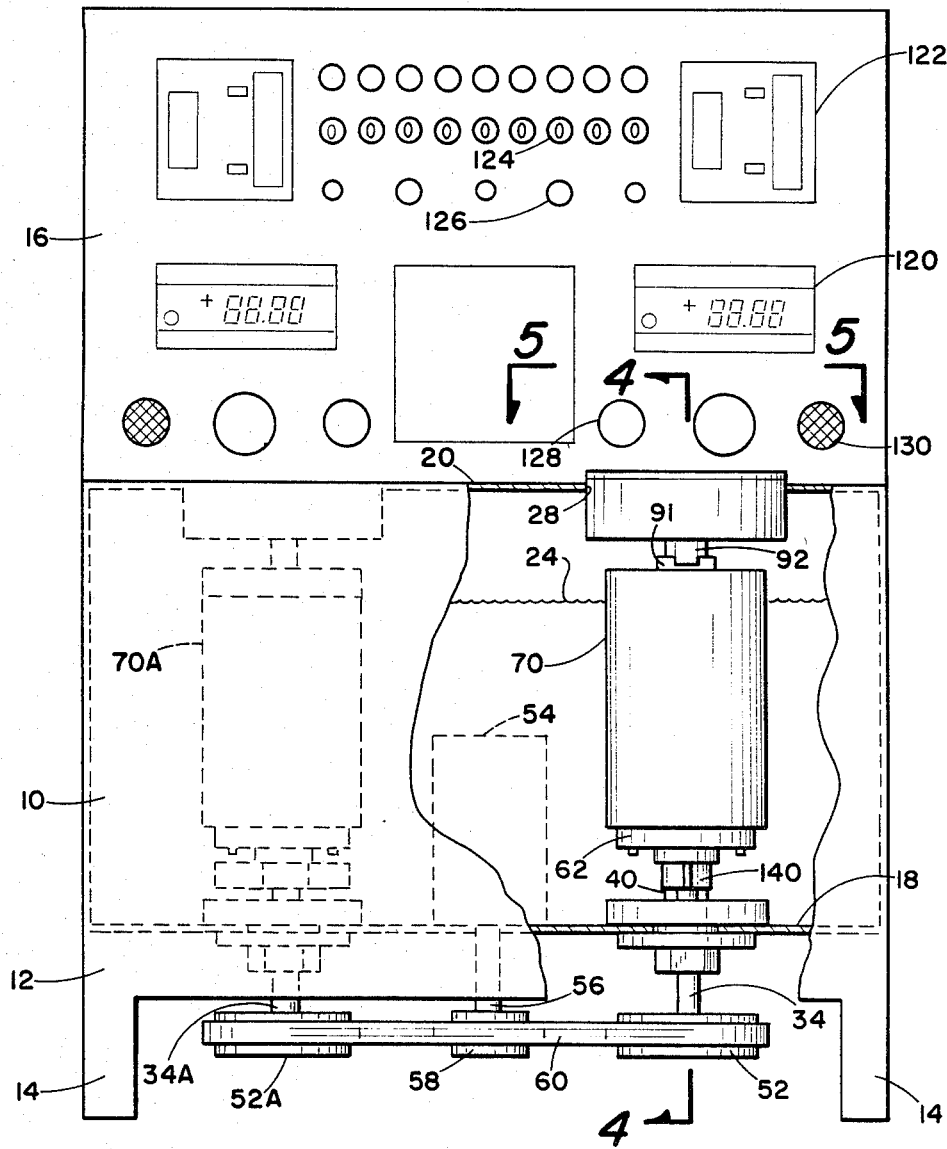
FIG. 2 is a front elevational view, shown partially cut away, of the apparatus of FIG. 1 and showing an embodiment of the invention in which two separate consistometer measurements may be simultaneously made.

Referring first to FIGS. 1, 2 and 3 a preferred embodiment of the invention is illustrated. The invention is shown as an entire unit capable of performing consistometer analysis. A vessel 10 is mounted on a base 12 having legs 14 by which it is supported on a workbench to provide proper height for a user. In addition to the vessel 10, supported on the base is a control panel 16.

Figure 4:
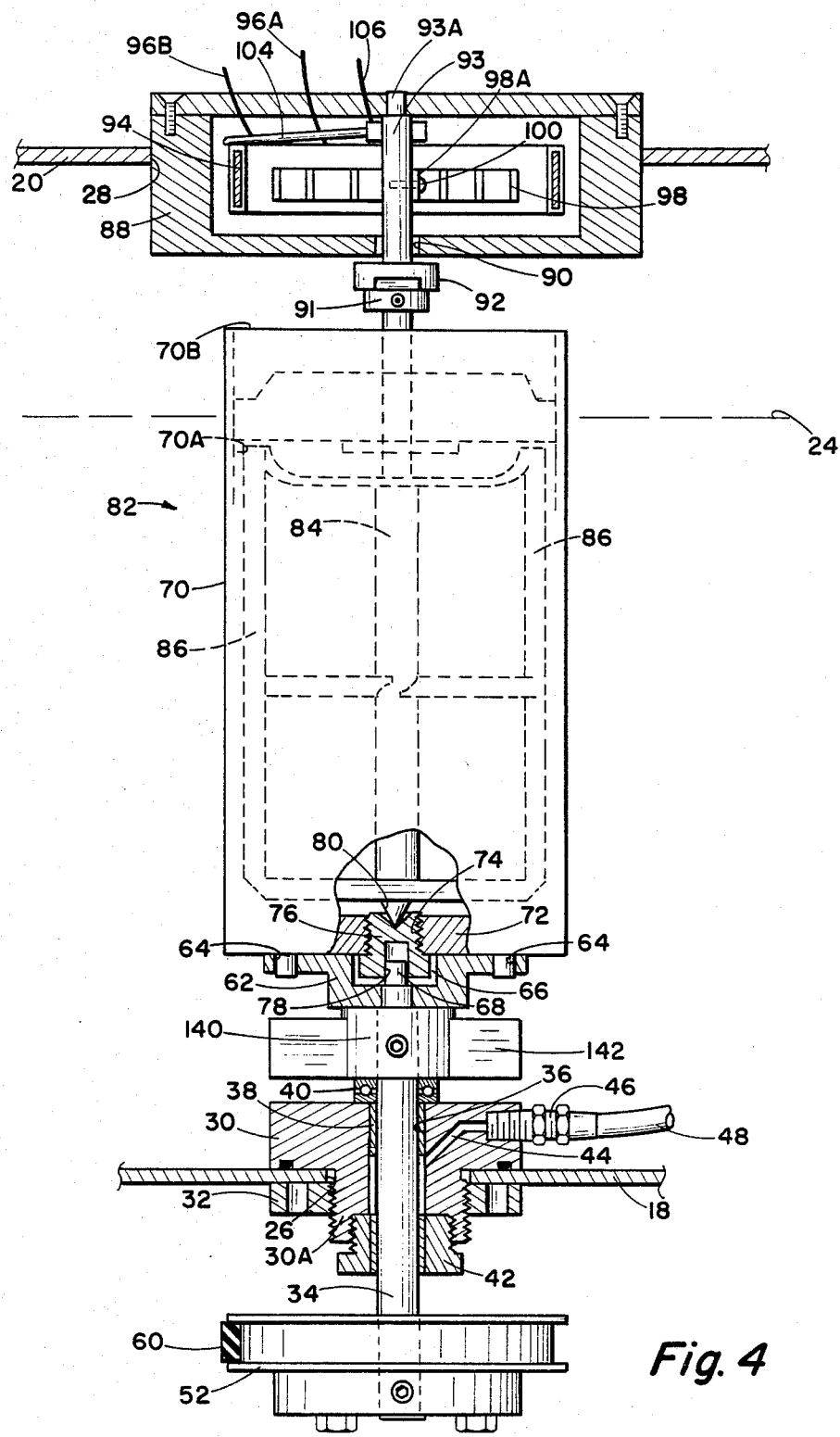
FIG. 4 is an enlarged elevational view shown primarially in cross-section, showing details of the driving mechanism, the slurry cup and the potentiometer cup.

The vessel 10 includes a bottom 18, a top 20 and four sidewalls 22. Vessel 10 is arranged to contain a liquid to the level indicated by the line 24. As shown in FIG. 4, the vessel bottom 18 has an opening 26 in it and the vessel top 20 has a larger diameter but vertically aligned opening 28. Received in the bottom opening 26 is a bearing block 30 having a reduced diameter lower externally threaded portion 30A extending through the opening 26. A nut member 32 which holds the bearing block onto the vessel bottom in a leakproof manner.

A vertical shaft 34 is received in an opening 36 formed in the bearing block which also receives a bushing 38. A thrust bearing 40 is received on shaft 34 to resist weight axially and downwardly applied on the shaft. A bushing 42 is received about shaft 34 and retains the bearing 40 within the bearing block. A passageway 44 in the bearing block is connected to a fitting 46 and a hose 48 which extends sealably through one of the sidewalls 22 of the vessel and to a zert fitting 50 attached to the backwall of the control panel 16 (See FIG. 1) and provides easy means for the lubrication of bearing 40 without requiring the fluid to be drained from the vessel 10.

Affixed to the lower end of shaft 34 is a shaft sheave 52. Positioned within the control panel 16 is an electric motor 54 having a vertically downwardly extending motor shaft 56 (See FIG. 2). Attached to the lower end of the motor shaft is a drive sheave 58. A belt 60 extends over sheaves 52 and 58 so that when motor 54 is energized shaft 34 is rotated.

The invention may be employed with a single shaft 34 extending from the vessel but in the illustrated arrangement the device is arranged so that two consistometer tests may be run simultaneously. For this purpose there is an additional shaft 34A and pulley 52A. Since the devices are the same, only one will be described but it is apparent from the structure of the device that it is equally usable with two or more consistometer measurement capabilities operated by the same motor and employing the same base, vessel and instrument panel. FIG. 3 shows diagramatically the arrangement of the sheaves and belt to show means whereby the two sheaves 52 and 52A are simultaneously driven.

Affixed to the upper end of shaft 34, as best seen in FIG. 4, is a flange 62. While the exact configuration of the flange may vary, in the illustrated arrangement it includes spaced apart openings 64 and an upper cylindrical recess 66 exposing a reduced diameter upward extension 68 of shaft 34.

Removeably received on flange 62 is a slurry cup 70 having cylindrical sidewalls and a bottom 72, the cup being opened at the top. A threaded opening 74 in the cup bottom receives a plug 76 having a lower recess 78 which, when the cup is in position on the flange as shown, receives the upward shaft extension 68. Plug 76 has a conical recess 80 in the upper surface. It can be seen that the cup is removeably supported on the flange 62 within the vessel 10 and in an arrangement wherein the cup is rotated about its cylindrical axis by power supplied by motor 54.

Received within the slurry cup 70 is a paddle generally indicated by the numeral 82, the paddle having a central vertical shaft 84 and vertical blades 86 which extends adjacent to but not in contact with the slurry cup sidewall interior cylindrical surface 70A. As previously mentioned, the vessel has liquid therein, the top of the liquid being at 24. The top 70B of the cup extends above the liquid level 24.

Received in the opening 28 in the vessel top 20 is a potentiometer cup 88 having an opening 90 in the bottom. Affixed to the upper end of paddle shaft 84 is a coupling member 91 which engages a mating coupling member 92 affixed to the lower end of a potentiometer shaft 93. The potentiometer shaft 93 is in effect, an upper extension of paddle shaft 84 and rotates in unison with it.

Figure 5:
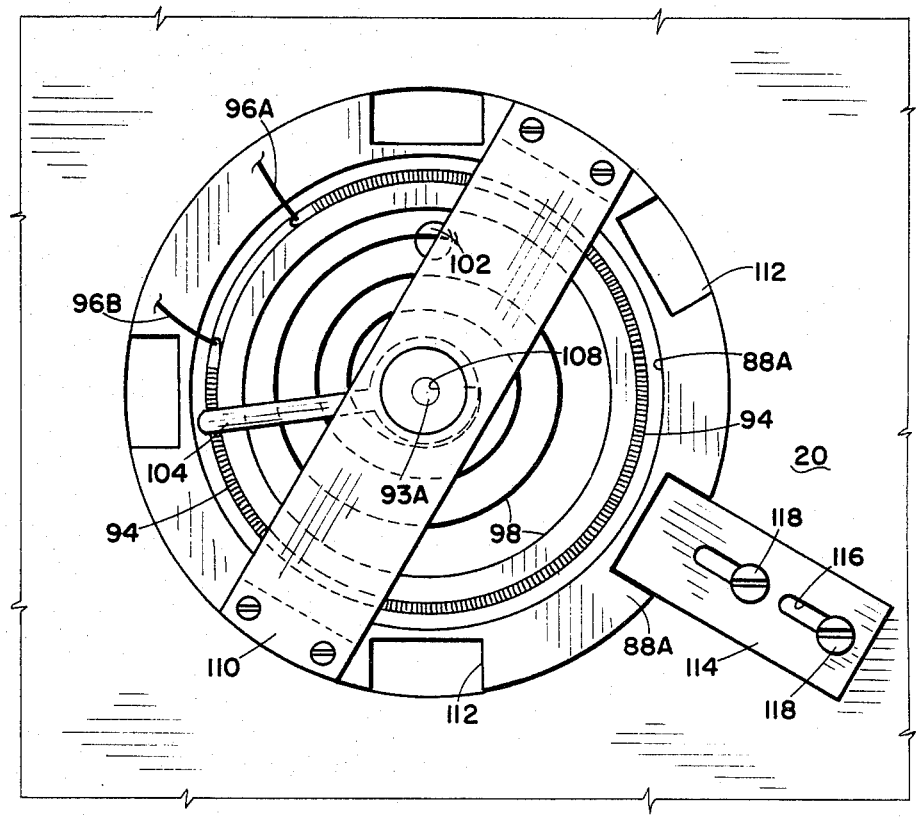
FIG. 5 is an enlarged top view of the potentiometer cup.

Positioned within cup 84 is a circular potentiometer 94. While it may be formed of a variety of constructions a preferred arrangement is that the potentiometer 94 is wire round about a tubular core. As shown in FIG. 5, the potentiometer 94 has leads 96A and 96B extending from it.

Received around the paddle shaft 84 is a coil spring 98, one end 98A of the spring being affixed to shaft 84, as best seen in FIG. 4, by means of a bolt 100. The other end of the spring is secured to the potentiometer cup 88 by means of a post 102, as best seen in FIG. 5. Thus the paddle and paddle shaft 84 are free to rotate but only within the limits imposed by spring 98.

Extending from potentiometer shaft 93 is a wiper arm 104 the outer end of which provides electrical contact with the potentiometer 94. The inner end of the wiper arm is connected to a lead 106. A highly flexible wire connects to lead 106 to reduce frictional drag on the rotation of potentiometer shaft 93 and paddle shaft 84. The lead is shown in FIG. 4 to illustrate the three leads which extend from the potentiometer.

The upper end 93A of the potentiometer shaft is of reduced diameter and is received by an opening 108 in a support bar 110.

As shown in FIG. 5 the potentiometer cup 88 has notches 112 in its peripherial surface which receives a locking bar 114 slideably retained on the vessel top. The locking bar has slots 116 receiving screws 118. By sliding the locking bar rearwardly the potentiometer cup can be rotated to any of the positions having a slot 112.

Figure 7:
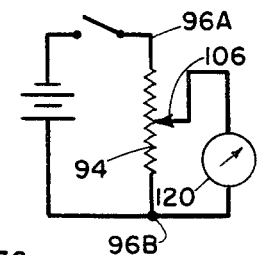
FIG. 7 is a rudimentary wiring diagram showing the method by which the consistency of a slurry is measured by a voltmeter.

As illustrated in the rudimentary wiring diagram of FIG. 7, a voltage potential is applied across leads 96A and 96B of potentiometer 94. A voltmeter 120 is connected between wiper arm lead 106 and lead 96B. Thus the volt meter 120 accurately indicates the position of the wiper arm 104.

To conduct a consistometer measurement of a slurry the potentiometer 88 is removed. Slurry cup 70 can then be removed through the opening 28 formed in the vessel top. The cup may then receive the slurry to be evaluated and reinstalled on flange 62 within the interior of the vessel the cup having paddle 82 therein. The potentiometer cup may then be inserted into position as shown in FIG. 4 with the flanges 91 and 92 in torque transmitting engagement with each other.

When motor 70 is energized there is a tendency for the slurry within the cup 70 also to rotate which is resisted by paddle 82. Thus a torque is applied to rotate paddle 82 proportional to the characteristics of the slurry, including viscosity and density. This torque tends to rotate shaft 84, and will rotate the shaft until the torque equals the tortional resistance imposed by spring 98. These forces always remain in balance and such tortional resistance is indicated by the position of the wiper arm 104 on potentiometer 94. Thus a voltage is applied to the volt meter 120 indicative of this tortional resistance which is a measurement of the consistency of the slurry within cup 70.

The control panel 16 includes the possibility of a variety of control features which may be used to facilitate the consistometer measurements. In the preferred practice of the invention the volt meter 120 is a digital instrument as shown in FIG. 2 to provide a more precise and errorproof indication of the detected slurry consistency. Other instruments which can be employed include timers 122, indicator lights 124, control switches 126, heat rate adjustment controls 128, audible alarms 130 and other devices including temperature measurement instruments.

In order to evaluate the consistency of slurries under different temperature conditions, the temperature of the liquid within vessel 10 is controlled by means of a heating element 132, as shown in FIG. 1. A voltage potential (not shown) is applied to the heating element. By means of the heat rate adjustment 128 the application of heat to the fluid within the vessel 10 may be controlled.

To more effectively transfer heat from the liquid with vessel 10 to the slurry within cup 70, an agitator member 140 is affixed to shaft 34 above bearing block 30 and below flange 62. Blades 142 extending from the agitator serve to stir and circulate the fluid within the vessel.

Figure 6:
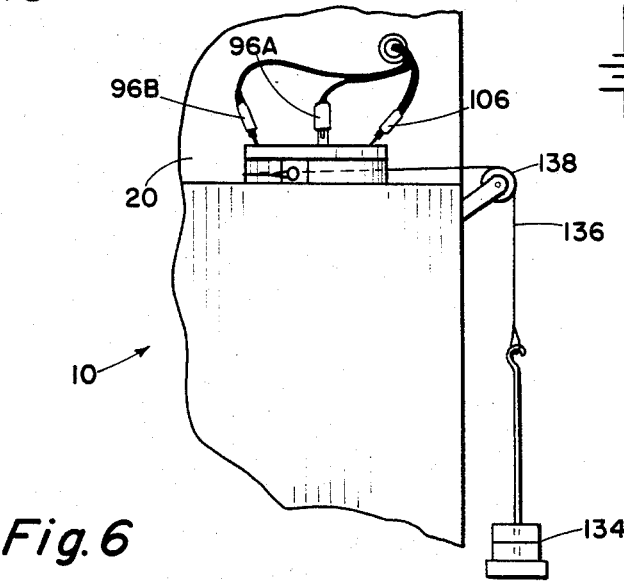
FIG. 6 is a diagramatic illustration of a method of calibrating the consistometer.

In order to calibrate the consistometer apparatus the arrangement of FIG. 6 may be employed. The shaft 84 equivalent to the paddle wheel shaft may be held stationary and a dead weight 134 applied by means of a cable 136 over a pully 138 to the peripherial surface of the potentiometer housing 88. This provides an accurate and expeditious way of measuring the deflection of the spring 98 within the potentiometer housing in response to a preselected and highly accurate torque which is directly proportional to the diameter of the potentiometer housing 88 and the weight 134. This measurement can be taken directly utilizing the same electrical circuit, volt meter, and so forth employed in the actual test for consistency and thus the instrument can be quickly and accurately calibrated.

While the invention has been described with a certain degree of particularity it is manifest that many changes may be made in the details of construction and arrangement of components without departing from the spirit and scope of the invention. The invention is not to be limited to the specific embodiments set forth herein for purposes of exemplification, but is to be limited only by the scope of the attached claim or claims, including the full range of equivalency to which each step or element thereof is entitled.

What is claimed is:

1. An apparatus for measuring the consistency of cement slurries comprising:
   a liquid containing vessel having a bottom, a top and sidewalls, the bottom and top having openings therein;
   a vertical shaft extending sealably through said container bottom opening;
   a flange affixed to the upper end of said shaft within said vessel and a sheave affixed to the lower end of said shaft exteriorly of said vessel;
   a motor mounted exteriorly of said vessel having a shaft extending therefrom, a sheave on the motor shaft and a belt between the sheaves whereby the motor rotates said flange;
   a slurry cup positionable within said container through said top opening therein, the slurry cup having a cylindrical sidewall, a bottom and an open top and including a pivot bearing recess in the cup interior bottom in alignment with the cup cylindrical axis;
   means engageable between the exterior of said cup bottom and said flange for removeably coupling the two whereby the cup is rotated coaxially with said shaft;
   a paddle removeably insertable within said cup, the paddle having an elongated vertical central paddle shaft portion and having a vertical blade portion in proximity to the cup interior cylindrical wall and having, on the lower end thereof, a downwardly extending conical bearing receivable in said cup pivot bearing recess, the paddle shaft and conical bearing being coaxial with said cup cylindrical axis;
   a potentiometer cup removeably supported within said opening in said vessel top and having an opening in the bottom thereof receiving said paddle shaft;
   a coiled spring received in said potentiometer cup in a plane perpendicular to said paddle shaft longitudinal axis, the spring being coiled about said paddle shaft and having one end affixed to said potentiometer cup and the other end affixed to said paddle shaft;
   a circular potentiometer element received in said potentiometer coaxial with and in a plane perpendicular to said paddle axis, the diameter of the potentiometer element being greater than said spring and less than said cup and having two electrical lead connections;
   an electrically conductive wiper arm extending from said paddle shaft and slideably engaging said potentiometer element, the wiper arm having an electrical lead connection;
   electrical heating means within said vessel, the vessel having liquid therein, the level of the liquid being below the top of said cup; and
   voltmeter means electrically connected with said potentiometer and wiper arm leads and a voltage source for indicating the position of said wiper arm which is responsive to the rotation of said paddle against the resilient restriction of said spring as said cup is rotated when said cup has a cement slurry therein, the rotational displacement of said paddle axis being indicative of the consistency of the cement slurry in said cup.

2. An apparatus for measuring the consistency of cement slurries according to claim 1 wherein said vessel has two spaced apart openings in said bottom and two spaced apart openings in said top, each bottom opening receiving a shaft, each shaft having a said flange at the upper end and a sheave at the lower end, said belt encompassing said motor sheave and both shaft sheaves, and including a said slurry cup, paddle, and potentiometer for each shaft, and including a said voltmeter for each potentiometer whereby two difference consistometer measurements may be made simultaneously.

3. An apparatus for measuring the consistency of cement slurries according to claim 1 including:
   an agitator member affixed to said shaft within said vessel and below said flange, having radially extending portions to provide circulation of fluid within the vessel.

* * * * *